(12) United States Patent
Que et al.

(10) Patent No.: US 8,956,381 B2
(45) Date of Patent: Feb. 17, 2015

(54) MECHANICALLY DETACHABLE VASO-OCCLUSIVE DEVICE

(75) Inventors: Like Que, Livermore, CA (US); Ann Huang, Fremont, CA (US); Esther Chang, Fremont, CA (US); Thazin Win, Fremont, CA (US); Stella Chu, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 839 days.

(21) Appl. No.: 11/942,952

(22) Filed: Nov. 20, 2007

(65) Prior Publication Data

US 2008/0119887 A1 May 22, 2008

Related U.S. Application Data

(60) Provisional application No. 60/866,586, filed on Nov. 20, 2006.

(51) Int. Cl.
*A61M 29/00* (2006.01)
*A61B 17/12* (2006.01)
*A61B 17/00* (2006.01)

(52) U.S. Cl.
CPC ..... *A61B 17/12022* (2013.01); *A61B 17/12113* (2013.01); *A61B 17/12145* (2013.01); *A61B 2017/00477* (2013.01); *A61B 2017/12054* (2013.01)
USPC .......................................................... 606/200

(58) Field of Classification Search
CPC .................. A61B 17/12022; A61B 17/12113; A61B 2017/00477; A61B 2017/12054
USPC ................................. 606/200, 158
See application file for complete search history.

(56) References Cited

U.S. PATENT DOCUMENTS

| 4,994,069 A | 2/1991 | Ritchart et al. |
| 5,122,136 A | 6/1992 | Guglielmi et al. |

(Continued)

FOREIGN PATENT DOCUMENTS

| EP | 0829236 A1 | 3/1998 |
| EP | 0832607 | 4/1998 |

(Continued)

OTHER PUBLICATIONS

PCT International Search Report for PCT/US2007/085201, Applicant Boston Scientific Scimed, Inc., Forms PCT/ISA/210 and 220, dated Aug. 1, 2008 (7 pages).

(Continued)

*Primary Examiner* — Thomas McEvoy
*Assistant Examiner* — Julie A Szpira
(74) *Attorney, Agent, or Firm* — Kacvinsky Daisak Bluni PLLC (57) ABSTRACT

A device for delivering an occlusive element includes an elongate sheath. A distal blocking member is located at the distal end of the elongate sheath and includes an aperture therein. An elongate releasing member is disposed within a lumen of the elongate sheath. The elongate releasing member includes a proximal end and a distal end with the distal end terminating in at least one retaining member. The device includes an occlusive element such as, for example, a vaso-occlusive coil that has a securing member located at a proximal end thereof. The securing member of the occlusive element passes through the aperture of the distal blocking member and the at least one retaining member is releasably secured to the securing member.

8 Claims, 5 Drawing Sheets

(56) References Cited

U.S. PATENT DOCUMENTS

| | | | |
|---|---|---|---|
| 5,226,911 A | 7/1993 | Chee et al. | |
| 5,250,071 A | 10/1993 | Palermo | |
| 5,304,194 A | 4/1994 | Chee et al. | |
| 5,382,259 A | 1/1995 | Phelps et al. | |
| 5,549,624 A | 8/1996 | Mirigian et al. | |
| 5,690,666 A | 11/1997 | Berenstein et al. | |
| 5,800,453 A | 9/1998 | Gia | |
| 5,800,455 A | 9/1998 | Palermo et al. | |
| 5,853,418 A | 12/1998 | Ken et al. | |
| 5,925,059 A | 7/1999 | Palermo et al. | |
| 6,280,457 B1 * | 8/2001 | Wallace et al. | 606/200 |
| 6,679,903 B2 | 1/2004 | Kurz | |
| 6,966,892 B2 | 11/2005 | Gandhi et al. | |
| 7,192,434 B2 * | 3/2007 | Anderson et al. | 606/200 |
| 7,691,124 B2 * | 4/2010 | Balgobin | 606/200 |
| 2002/0165569 A1 | 11/2002 | Ramzipoor et al. | |
| 2004/0034363 A1 | 2/2004 | Wilson et al. | |
| 2004/0111095 A1 | 6/2004 | Gordon et al. | |
| 2005/0043755 A1 * | 2/2005 | Wilson et al. | 606/200 |
| 2005/0222605 A1 | 10/2005 | Greenhalgh et al. | |
| 2005/0234505 A1 | 10/2005 | Diaz et al. | |
| 2006/0025801 A1 * | 2/2006 | Lulo et al. | 606/200 |
| 2006/0025802 A1 * | 2/2006 | Sowers | 606/200 |
| 2006/0025803 A1 | 2/2006 | Mitelberg et al. | |
| 2006/0116714 A1 * | 6/2006 | Sepetka et al. | 606/200 |
| 2006/0276825 A1 | 12/2006 | Mitelberg et al. | |
| 2006/0276826 A1 | 12/2006 | Mitelberg et al. | |
| 2006/0276834 A1 | 12/2006 | Balgobin et al. | |
| 2007/0021775 A1 * | 1/2007 | Vrba et al. | 606/200 |
| 2007/0055302 A1 * | 3/2007 | Henry et al. | 606/200 |
| 2007/0179520 A1 * | 8/2007 | West | 606/200 |
| 2007/0239192 A1 * | 10/2007 | Litzenberg et al. | 606/191 |
| 2012/0041472 A1 * | 2/2012 | Tan et al. | 606/200 |

FOREIGN PATENT DOCUMENTS

| | | |
|---|---|---|
| EP | 1621148 A1 | 2/2006 |
| EP | 1621149 A1 | 2/2006 |
| EP | 1738697 | 1/2007 |
| EP | 1738698 A2 | 1/2007 |
| EP | 1797833 A1 | 6/2007 |
| WO | 2006058042 | 6/2006 |

OTHER PUBLICATIONS

PCT Written Opinion of the International Search Authority for PCT/US2007/085201, Applicant Boston Scientific Scimed, Inc., Form PCT/ISA/237, dated Aug. 1, 2008 (6 pages).

PCT International Search Report for PCT/US2007/085182, Applicant Boston Scientific Scimed, Inc., Forms PCT/ISA/210 and 220, dated Apr. 16, 2008 (5 pages).

PCT Written Opinion of the International Search Authority for PCT/US2007/085182, Applicant Boston Scientific Scimed, Inc., Form PCT/ISA/237 dated Apr. 16, 2008 (7 pages).

PCT International Search Report for PCT/US2007/085205, Applicant Boston Scientific Scimed Inc., Forms PCT/ISA/210 and 220, dated Apr. 16, 2008 (5 pages).

PCT Written Opinion of the International Search Authority for PCT/US2007/085205, Applicant Boston Scientific Scimed, Inc., Form PCT/ISA/237 dated Apr. 16, 2008 (6 pages).

PCT International Search Report for PCT/US2007/085198, Applicant Boston Scientific Scimed, Inc., Forms PCT/ISA/210 and 220, dated May 16, 2008 (5 pages).

PCT Written Opinion of the International Search Authority for PCT/US2007/085198 Applicant Boston Scientific Scimed, Inc., Form PCT/ISA/237 dated May 16, 2008 (10 pages).

Non final Office Action dated Apr. 16, 2009, for related U.S. Appl. No. 11/942,890, Inventors Like Que et al., filed Nov. 20, 2007 (19 pages).

Non final Office Action dated Apr. 16, 2009, for related U.S. Appl. No. 11/942,913, Inventors Like Que et al., filed Nov. 20, 2007 (21 pages).

Non final Office Action dated Apr. 16, 2009, for related U.S. Appl. No. 11/942,929, Inventors Thazin Win et al., filed Nov. 20, 2007 (18 pages).

Office Action for EP Application EP 07864641.1, Applicant Boston Scientific Limited, dated Dec. 15, 2010 (5 pages).

Papers from File History for U.S. Appl. No. 11/942,913, filed Nov. 20, 2007, Inventor Like Que et al., including (55 pages): Response to non-final office action dated Apr. 16, 2009, response submitted on Jul. 1, 2009; Final Rejection dated Nov. 27, 2009; Response to Final Rejection dated Nov. 27, 2009, response submitted on Jan. 21, 2010; Non-final Office action dated Sep. 1, 2010; Response to non-final office action dated Sep. 1, 2010, response submitted on Oct. 26, 2010; Non-final office action dated Feb. 15, 2011.

Papers from File History for U.S. Appl. No. 11/942,929, filed Nov. 20, 2007, Inventor Thazin Win et al., including (46 pages): Response to non-final office action dated Apr. 16, 2009, response submitted on Jul. 1, 2009; Final Rejection dated Oct. 29, 2009; Response to Final Rejection dated Oct. 29, 2009, response submitted on Jan. 22, 2010; Non-final Office action dated Jul. 19, 2010; Response to non-final office action dated Jul. 19, 2010, response submitted on Oct. 13, 2010; Final Rejection dated Jan. 12, 2011.

Papers from file history for U.S. Appl. No. 11/942,890, filed Nov. 20, 2007, Inventor Like Que et al., including (53 pages): Response to non-final office action dated Apr. 16, 2009, response submitted on Jul. 1, 2009; Final Rejection dated Oct. 29, 2009; Response to Final Rejection dated Oct. 29, 2009, response submitted on Jan. 22, 2010; Non-final Office action dated Jul. 8, 2010; Response to non-final office action dated Jul. 8, 2010, response submitted on Oct. 4, 2010; Final Rejection dated Dec. 22, 2010 Response to Final Rejection dated Dec. 22, 2010, response submitted on Mar. 9, 1819.

* cited by examiner

MECHANICALLY DETACHABLE VASO-OCCLUSIVE DEVICE

RELATED APPLICATION DATA

The present application claims the benefit under 35 U.S.C. §119 to U.S. provisional patent application Ser. No. 60/866,586, filed Nov. 20, 2006. The foregoing application is hereby incorporated by reference into the present application in its entirety.

FIELD OF THE INVENTION

The field of the invention generally relates to systems and delivery devices for implanting vaso-occlusive devices for establishing an embolus or vascular occlusion in a vessel of a human or veterinary patient.

BACKGROUND OF THE INVENTION

Vaso-occlusive devices or implants are used for a wide variety of reasons, including treatment of intra-vascular aneurysms. A common vaso-occlusive device takes the form of a soft, helically wound coil formed by winding a platinum (or platinum alloy) wire strand about a primary mandrel. The relative stiffness of the coil will depend, among other things, on its composition, the diameter of the wire strand, the diameter of the primary mandrel, and the pitch of the primary windings. The coil is then wrapped around a larger, secondary mandrel, and again heat treated to impart a secondary shape. For example, U.S. Pat. No. 4,994,069, issued to Ritchart et al., describes a vaso-occlusive coil that assumes a linear, helical primary shape when stretched for placement through the lumen of a delivery catheter, and a folded, convoluted secondary shape when released from the delivery catheter and deposited in the vasculature.

In order to deliver the vaso-occlusive coils to a desired site, e.g., an aneurysm, in the vasculature, it is well-known to first position a small profile, micro-catheter at the site using a steerable guidewire. Typically, the distal end of the micro-catheter is provided, either by the attending physician or by the manufacturer, with a selected pre-shaped bend, e.g., 45°, 90°, "J", "S", or other bending shape, depending on the particular anatomy of the patient, so that it will stay in a desired position for releasing one or more vaso-occlusive coil(s) into the aneurysm once the guidewire is withdrawn. A delivery or "pusher" wire is then passed through the micro-catheter, until a vaso-occlusive coil coupled to a distal end of the pusher wire is extended out of the distal end opening of the micro-catheter and into the aneurysm. The vaso-occlusive device is then released or "detached" from the end pusher wire, and the pusher wire is withdrawn back through the catheter. Depending on the particular needs of the patient, another occlusive device may then be pushed through the catheter and released at the same site.

One known way to release a vaso-occlusive coil from the end of the pusher wire is through the use of an electrolytically severable junction, which is a small exposed section or detachment zone located along a distal end portion of the pusher wire. The detachment zone is typically made of stainless steel and is located just proximal of the vaso-occlusive device. An electrolytically severable junction is susceptible to electrolysis and disintegrates when the pusher wire is electrically charged in the presence of an ionic solution, such as blood or other bodily fluids. Thus, once the detachment zone exits out of the catheter distal end and is exposed in the vessel blood pool of the patient, a current applied to the conductive pusher wire completes a circuit with an electrode attached to the patient's skin, or with a conductive needle inserted through the skin at a remote site, and the detachment zone disintegrates due to electrolysis.

U.S. Pat. No. 5,122,136 issued to Guglielmi, et al. discloses a device in which a portion of the guidewire connected between the tip and the body of the guidewire is comprised of stainless steel and exposed to the bloodstream so that upon continued application of a positive current to the exposed portion, the exposed portion is corroded away at least at one location and the tip is separated from the body of the guidewire. The guidewire and a microcatheter are thereafter removed leaving the guidewire tip embedded in the thrombus formed within the vascular cavity.

One perceived disadvantage with vaso-occlusive devices that are deployed using electrolytic detachment is that the electrolytic process requires a certain amount of time to elapse to effectuate release of the vaso-occlusive element. This time lag is also a perceived disadvantage for vaso-occlusive delivery devices that utilize thermal detachment mechanisms. U.S. Pat. No. 6,966,892 issued to Gandhi, et al. discloses a vaso-occlusive device that uses a thermal detachment system.

Another detachment modality used to deploy vaso-occlusive elements uses mechanical detachment. U.S. Pat. No. 5,800,453 issued to Gia discloses embolic coils that have a receiving slot on one end. A catheter control wire or pusher guidewire having a hook which engages the coil's receiving slot is used as a coil pusher to eject the coil at the chosen site. The coils may also be placed within the lumen with a catheter in a nose-to-tail fashion and pushed into the body lumen. Pushing the coil assembly via the pusher from the distal end of the catheter body uncouples the distal most coil.

Another example of a mechanical detachment system is disclosed in U.S. Pat. No. 5,800,455 issued to Palermo et al. Palermo et al. discloses a delivery system that includes a coil having a clasp located at one end. The clasp includes a passageway for a control wire. The clasp interlocks with another clasp located on a distal end of a pusher member. The control wire is withdrawn in the proximal direction to release the coil.

Still other mechanical detachments systems have been proposed that use a fiber segment that is pulled in the proximal direction to decoupled the fiber from the embolic coil device. Examples of these systems may be found in U.S. Patent Application Publication Nos. 2006/0025803 A1 (coiled fiber), 2006/0025802 A1 (U-shaped fiber), and 2006/0025801 A1 (detachment filament).

One problem with certain existing mechanical detachment systems is that the junction between the embolic element and the releasing member moves during the detachment process which may adversely impact the placement of the embolic element within the aneurysm. Another complication is that mechanical detachment systems tend to have a stiff main section that complicates accurate placement of the delivery system at the desired location, i.e., a stiff section of the pusher wire or the pusher wire/coil junction can cause a pre-shaped micro-catheter to kick back or recoil from the aneurysm. Mechanical detachment systems also are perceived by physicians as being harder to use than other devices. In addition, certain mechanical detachment systems may jeopardize the integrity of the embolic element (e.g. coil) after detachment.

There thus is a need for a vaso-occlusive delivery system that utilizes mechanical detachment yet does not suffer from the aforementioned deficiencies. Such a system should be easy to use yet provide for consistent detachment of embolic elements in the desired location. Moreover, the delivery system should be able to release the embolic element without extensive movement resulting from the detachment operation.

SUMMARY

In one embodiment, a device for delivering an occlusive element includes an elongate sheath having a distal end and a proximal end and a lumen extending between the distal and proximal ends. A distal blocking member is located at the distal end of the elongate sheath and includes an aperture therein. An elongate releasing member is disposed within the lumen of the elongate sheath. The elongate releasing member includes a proximal end and a distal end with the distal end terminating in at least one retaining member. The device includes an occlusive element such as, for example, a vaso-occlusive coil that has a securing member located at a proximal end thereof. The securing member of the occlusive element passes through the aperture of the distal blocking member and the at least one retaining member is releasably secured to the securing member.

The at least one retaining member may take the form of a wire or the like that includes a bent or curved segment that is used to hook the securing member on the occlusive element. For example, in one aspect, two retaining members that are bent or curved are used to grasp the securing member on the occlusive element. The retaining member(s) may be formed from a substantially elastic material.

In another embodiment, a locking member is disposed on a proximal region of the elongate releasing member. The locking member prevents both proximal and distal movement of the elongate releasing member so as to (1) prevent premature detachment, and (2) the locking member acts as a safety feature that prevents the elongate releasing member from poking or damaging the delivery site (e.g., aneurysm). For example, the locking member may be slidable along the elongate releasing member in a distal direction but not in a proximal direction. In this regard, the locking member may be loaded onto the proximal end of the elongate releasing member and advanced until the locking member engages with the elongate sheath.

In another aspect of the invention, a method of deploying a vaso-occlusive coil includes positioning a vaso-occlusive coil adjacent to a deployment site, the vaso-occlusive coil being held distally with respect to a distal end of an elongate sheath. The occlusive coil is releasably secured to an elongate releasing member passing through the elongate sheath by at least one retaining member. By first separating the locking member from the elongated sheath, the elongate releasing member can be pulled proximally relative to the elongate sheath so as to release the occlusive coil from the at least one retaining member.

In still another aspect of the invention, a method of loading a vaso-occlusive coil on a deployment device includes providing an elongate sheath and an elongate releasing member slidable within a lumen of the elongate sheath. The elongate releasing member includes at least one retaining member on a distal end thereof. The elongate sheath includes a distal blocking member located at the distal end of the elongate sheath. The distal blocking member includes an aperture therein. The elongate releasing member is advanced distally, or back loaded proximally, through the lumen of the elongate sheath such that the at least one retaining member extends distally of the distal blocking member. The vaso-occlusive coil is then secured to the at least one retaining member. The elongate releasing member is then retracted proximally to position the at least one retaining member proximal relative to the distal blocking member. A locking member is used to fix the elongated releasing member to the elongated sheath to prevent both distal and proximal movement of the elongate releasing member relative to the elongate sheath.

BRIEF DESCRIPTION OF THE DRAWINGS

FIG. 6 illustrates a partial cross-sectional view of the distal end of the delivery device. FIG. 6 illustrates the process of loading a vaso-occlusive coil onto the elongate releasing member.

FIG. 9 is a partial cross-sectional view of the distal end of the delivery device. FIG. 9 illustrates the coil being deployed from the elongate sheath by proximal retraction of the elongate releasing member.

DETAILED DESCRIPTION OF THE ILLUSTRATED EMBODIMENTS

Figure 1:
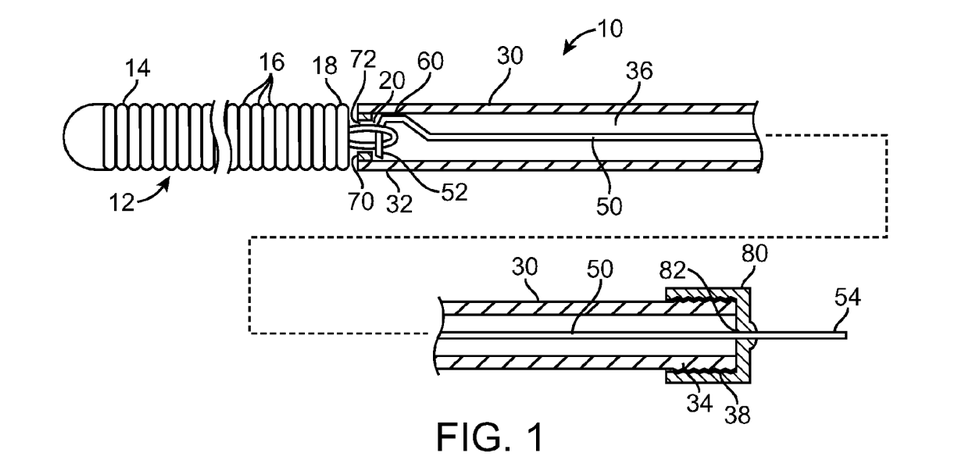
FIG. 1 is a partial cross-sectional view of a device for delivering an occlusive element according to one embodiment.

FIG. 1 illustrates a device 10 for delivering an occlusive element 12 to a vascular space such as, for example, aneurysm. The occlusive element 12 may be formed as a vaso-occlusive coil 14 formed from a plurality of coil windings 16. When manufacturing the vaso-occlusive coil 14, the coil material is wound into a coil shape, which will typically be linear. Generally speaking, the coil 14 is a metallic coil made from a platinum alloy or a super-elastic alloy such as titanium/nickel alloy, known as "NITINOL." The diameter of the wire used in the production of the coils 14 may fall in the range of about 0.00025 inches to about 0.006 inches. The coil 14 may have a primary diameter of between about 0.003 and about 0.025 inches, but for most neurovascular applications, a diameter between about 0.008 to about 0.018 inches provides sufficient hoop strength to hold the coil 14 in place within the chosen body site, lumen, or cavity, without substantially distending the wall of the site and without moving from the site as a result of the repetitive fluid pulsing found in the vascular system.

The axial length of the coil wire will usually fall in the range of around 0.5 to around 100 cm, more usually around 2.0 to 40 cm. Of course, all of the dimensions provided above should be viewed only as guidelines, and the invention, in its broader aspects, should not be limited thereto. Dimensions that are suitable for use in occluding sites within the human body are included in the scope of this invention.

Depending on the desired therapeutic effect and the shape of the site to be treated, the coil 14 may later be treated or accessorized in numerous ways in order to enhance its therapeutic effect. The coil 14 may be made to form various secondary shapes, often through the use of heat treatment, that may be better suited to fill a particular treatment site, as disclosed in U.S. Pat. Nos. 5,853,418 and 6,280,457, the entireties of which are expressly incorporated herein by reference. Alternatively, the coil 14 may have little or no shape after introduction into the vascular space, as disclosed in U.S. Pat. No. 5,690,666, the entirety of which is expressly incorporated by reference herein. In addition, external materials may be added to the outside of the coil 14 in an effort to increase its thrombolytic properties. These alternative embodiments are disclosed in U.S. Pat. Nos. 5,226,911, 5,304,194, 5,549,624, 5,382,259, and 6,280,457, the entireties of which are expressly incorporated herein by reference.

Figure 2:
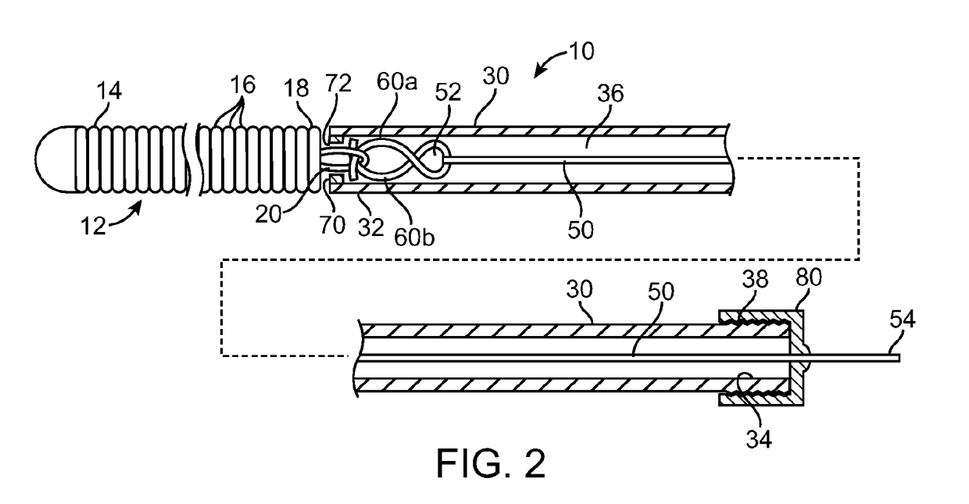
FIG. 2 is a partial cross-sectional view of a device for delivering an occlusive element according to another embodiment.

As best seen in FIGS. 1 and 2, the proximal end 18 of the coil 14 includes a securing member 20. The securing member 20 may be formed as a closed hoop or ring as is illustrated in FIG. 1. Alternatively, the securing member 20 may be formed in an open configuration such as a hook or the like (not shown). The hoop or ring form of the securing member 20 in FIGS. 1 and 2 has its two ends fixedly secured to a proximal end 18 of the coil 14. In one embodiment, the securing member 20 may be formed integrally with the coil 14. In this regard, the securing member 20 may be formed from a proximal winding of the coil 14. For example, the proximal winding may be looped back upon itself and optionally bonded to one or more windings 16 to form the closed securing member 20. Alternatively, the securing member 20 may be formed separately from the coil 14. For example, the securing member 20 may be formed from a thin metal wire filament such as platinum, NITINOL, titanium, stainless steel, and metallic alloys. Alternatively, the securing member 20 may be formed form a polymer-based material such as PTFE, polypropylene, PEEK, and the like. The separate securing member 20 may then be jointed to the proximal end 18 of the coil 14 either by tying or through a bonding operation. For example, an adhesive material, soldering, or a weld may be used to fixedly attach the securing member 20 to the proximal 18 of the coil 14.

The delivery device 10 also includes an elongate sheath 30 having a distal end 32, a proximal end 34, and a lumen 36 therebetween. The elongate sheath 30 may be formed from a flexible yet lubricious material such as polyimide, polytetrafluoroethylene (PTFE), polyetheretherketone (PEEK), fluorinated ethylene propylene (FEP), or the like. The elongate sheath 30 generally has a length that permits the same to be advanced intravascularly to the site of interest. For example, the elongate sheath 30 has a length to permit the distal end 32 to be positioned adjacent to the delivery site (e.g., aneurysm) while the proximal end 34 is positioned outside the patient's body. A typical range of lengths for the elongate sheath 30 may include between about 1.25 meters to about 2.0 meters. The elongate sheath 30 may be formed form non-polymer materials. For example, one or more segments may be formed from metal hypotube formed from stainless steel, NITINOL, and the like.

Still referring to FIG. 1, an elongate releasing member 50 is disposed within the lumen 36 of the elongate sheath 30. The elongate releasing member 50 has a distal end 52 and a proximal end 54. The elongate releasing member 50 is formed from a flexible yet sturdy material that provides sufficient columnar strength to avoid breakage during the deployment process (described in more detail below). For example, the elongate releasing member 50 may be formed from one or more wires or filaments. The wire(s) may be formed from a metal or alloy such as NITINOL, titanium, stainless steel or the like. Alternatively, filament(s) may be formed from a polymer material such as polyimide, polypropylene, polyetheretherketone (PEEK), polytetrafluoroethylene (PTFE), and the like.

Referring to the embodiment of FIG. 1, the distal end 52 of the elongate releasing member 50 terminates in at least one retaining member 60. The at least one retaining member 60 may be integrally formed with the elongate releasing member 50 as is shown in FIG. 1 or, alternatively, the at least one retaining member 60 may be bonded, jointed, or otherwise coupled to the distal end of the distal end 52 of the elongate releasing member 50. FIG. 1 illustrates a single retaining member 60 in the form of a bent segment of wire. It should be understood, however, that the retaining member 60 may be formed with other geometric profiles. For example, the retaining member 60 may be formed from a curved or hooked segment of wire.

As seen in FIG. 1, the retaining member 60 passes through the securing member 20 and prevents distal movement (or release) of the securing member 20 and coil 14. The retaining member 60 thus couples the coil 14 to the elongate releasing member 50. Still referring to FIG. 1, a distal blocking member 70 is positioned at the distal end 32 of the elongate sheath 30. The distal blocking member 70 may be secured inside the lumen 36 of the elongate sheath 30 at the distal end. The distal blocking member 70 may be secured to the interior of the elongate sheath 30 by bonding a short segment of tubing formed from, for instance, a metal or polymer material. The distal blocking member 70 may be secured to the distal end 32 using an adhesive material. Alternatively, the distal blocking member 70 may be created by welding the same tubing material with a smaller ID to the interior lumen 36 of the elongate sheath 30. Alternatively, the distal blocking member 70 may be secured by press fitting, or by heat forming the elongated sheath tip into the desired blocking structure.

As seen in FIG. 1, the distal blocking member 70 includes an aperture 72 that acts as an access passageway to the lumen 36 of the elongate sheath 30. Accordingly, one object of the distal blocking member 70 is to reduce the effective size of the lumen 36. The distal blocking member 70 thus prevents the coil 14 from moving in the proximal direction and into the elongate sheath 30. The distal blocking member 70 serves as an abutment against which the coil 14 contact to prevent pull back of the coil 14 into the elongate sheath 30. The distal blocking member 70 also prevents the elongate releasing member 50 from moving out from the elongate sheath 30. The aperture 72 is sized to allow passage of all or at least a portion of the securing member 20 into the lumen 36 of the elongate sheath 30.

Figure 4A:
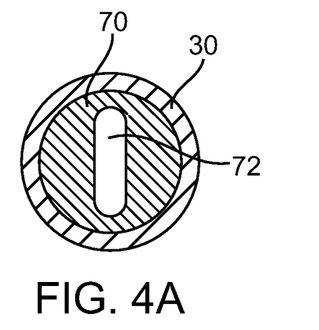
FIG. 4A is a cross-sectional end view of the elongate sheath and blocking member according to one embodiment.
Figure 4B:
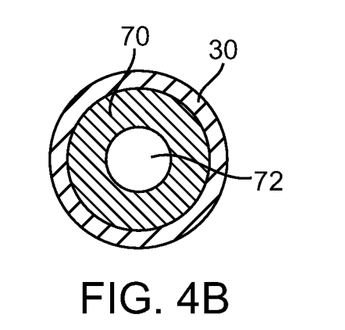
FIG. 4B is a cross-sectional end view of the elongate sheath and blocking member according to another embodiment.
Figure 4C:
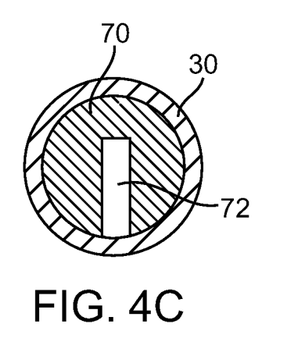
FIG. 4C is a cross-sectional end view of the elongate sheath and blocking member according to another embodiment.
Figure 4D:
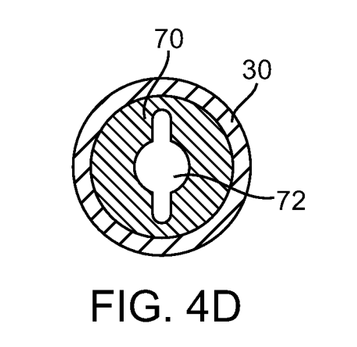
FIG. 4D is a cross-sectional end view of the elongate sheath and blocking member according to another embodiment.

FIGS. 4A, 4B, 4C, and 4D illustrate four cross-sectional views of different apertures 72 that may be formed in the distal blocking member 70. As shown in FIG. 4A, the aperture 72 may be formed in the manner of a slot that is centrally disposed in the distal blocking member 70. FIG. 4B illustrates an embodiment wherein the aperture 72 is formed as a circular passageway within the distal blocking member 70. FIG. 4C illustrates yet another alternative embodiment wherein the aperture 72 is formed from slot giving the distal blocking member a u-shaped profile. FIG. 4D illustrates another aperture 72 that includes a circular portion as well as a slotted portion. The combination of the two forms a keyhole-like structure.

Figure 10:
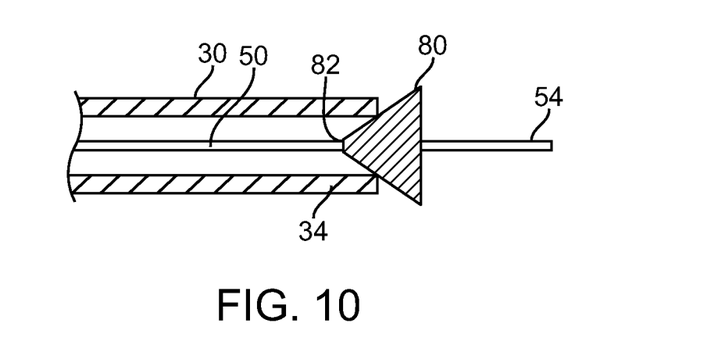
FIG. 10 is cross-sectional view of the proximal end of an elongate sheath showing the locking member engaged with a proximal end thereof.

Referring to FIGS. 1, 2 and 10, the elongate releasing member 50 traverses the length of the elongate sheath 30 and terminates at a proximal end 54 that is located external to the proximal end 34 of the elongate sheath 30. The delivery device 10 includes a locking member 80. The locking member 80 includes an aperture 82 through which the elongate releasing member 50 passes. In one embodiment, the locking member 80 is slidable along the length of the elongate releasing member 50. After loading the coil 14 on the retaining member 60, the locking member 80 may be advanced distally over the proximal end 54 of the elongate releasing member 50 until the locking member 80 reaches the proximal end 34 of the elongate sheath 30 (see, e.g., FIGS. 5A-C and 10). Once in position, the locking member 80 may be secured to the elongate member 50. The securing of the locking member 80 may be accomplished by bonding the locking member 80 directly to the elongate releasing member 50 using, for example, an adhesive, solder, or weld. Alternatively, the locking member 80 may be crimped to form a friction fit between the locking member 80 and elongate releasing member 50. The locking member 80 prevents further distal advancement of the elongate releasing member 50 with respect to the elongate sheath 30.

As shown in FIGS. 1, 2, and 5A-5C, locking member 80 may be secured to the elongate sheath 30 by the use of threads 38 formed about the periphery of the proximal end 34 of the elongate sheath 30. The locking member 80 can thus be releasably secured to the elongate sheath 30 to prevent relative movement between the elongate releasing member 50 and the elongate sheath 30.

Figure 5A:
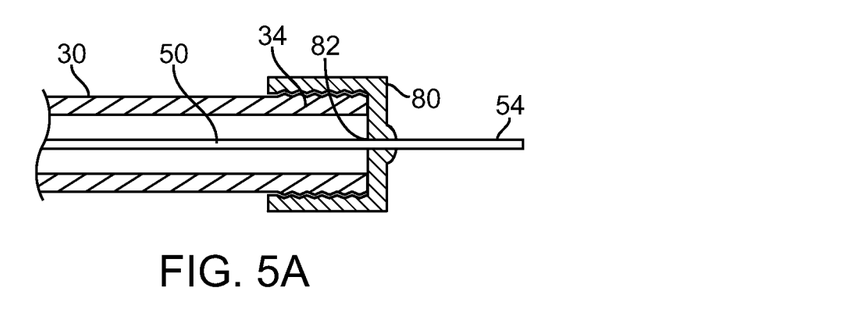
FIG. 5A is a cross-sectional view of the proximal end of the elongate sheath. A locking member is illustrated gripping the elongate releasing member so as to prevent movement of the elongate releasing member in both the distal and proximal directions.
Figure 5B:
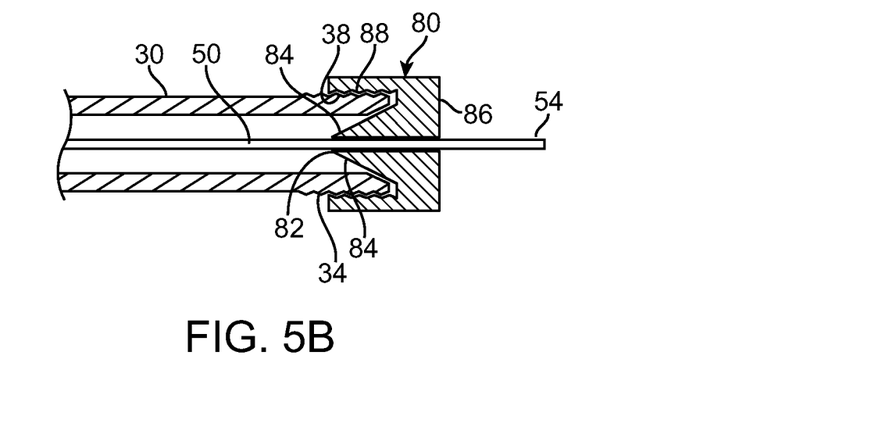
FIG. 5B is a cross-sectional view of the proximal end of the elongate sheath. A locking member according to another embodiment is illustrated gripping the elongate releasing member so as to prevent movement of the elongate releasing member in both the distal and proximal directions.
Figure 5C:
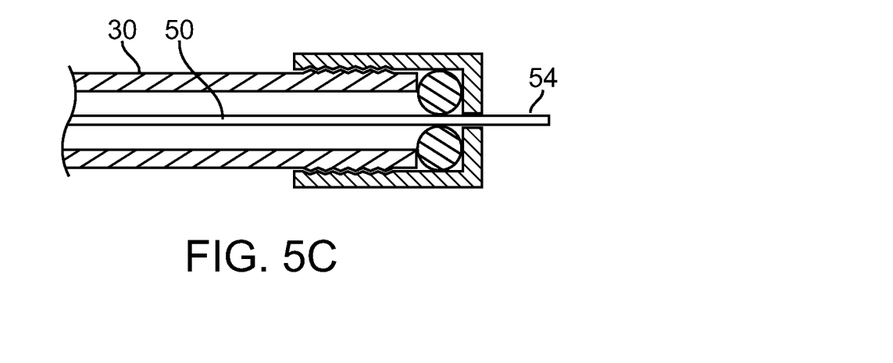
FIG. 5C is a cross-sectional view of the proximal end of the elongate sheath. A locking member and O-ring are illustrated gripping the elongate releasing member so as to prevent movement of the elongate releasing member in both the proximal and distal directions.

The locking member 80 thus prevents the coil 14 and retaining member(s) 60 from moving both proximally and distally with respect to the distal end 32 of the elongate sheath 30. In this regard, the locking member 80 prevents the early or premature disengagement between the coil 14 and the elongate releasing member 50. It also prevents the elongate releasing member 50 from moving distally wherein the elongate releasing member 50 could inadvertently poke the aneurysm 100.

FIGS. 5A and 5B illustrate cross-sectional views of the proximal end 34 of the elongate sheath 30 with the locking member 80 in place according to one embodiment. In FIG. 5A, the locking member 80 passes through an aperture 82. The locking member 80 includes a gripping member 84 located at the proximal end of the locking member 80. The gripping member 84 grips the elongate releasing member 50 once the locking member 80 is advanced within the lumen 36 of the elongate sheath 30. The holding strength of the gripping member 84 is such that a physician cannot advance the elongate releasing member 50 with respect the elongate sheath 30.

While movement in the distal and proximal directions is prevented, the locking member 80 can be released from the elongate sheath 30 in response to pulling (or unscrewing) the releasing member 50 in the proximal direction. In this manner, the coil 14 may be deployed by first releasing locking member 80 from the proximal end 34 of the elongate sheath 30 and retracting the elongate releasing member 50 in the proximal direction relative to the elongate sheath 30.

FIG. 5B illustrates an alternative embodiment of the locking member 80. In this alternative embodiment, the locking member 80 is formed as a proximal cap 86 that has internal grooves 88 for engaging with threads 38 formed about the periphery of the proximal end 34 of the elongate sheath 30. By tightening the cap 86, the gripping member 84 progressively tightens down on the elongate releasing member 50 until it is locked in place relative to the elongate sheath 30. For deployment, the cap 86 is unscrewed in the opposite direction to release the gripping member 84 from the elongate releasing member 50.

FIG. 5C illustrates yet another alternative embodiment of the locking member 80. As in the prior embodiment, the locking member 80 is a proximal cap 86 that has internal grooves 88 for engaging with threads 38 formed on the periphery of the proximal end 34 of the elongate sheath 30. In this embodiment, an O-ring 81 is positioned proximal relative to the end 34 of the elongate sheath. The O-ring may be made of a compressible material such as, for instance, rubber or the like. The O-ring is compressed between the cap 86 and the proximal end of the elongate sheath 34, thereby causing radial expansion of the O-ring 81. The expansion of the O-ring 81 causes the same to engage with the elongate releasing member 50 so as to prevent relative movement between the elongate releasing member 50 and the elongate sheath 30.

Figure 3:
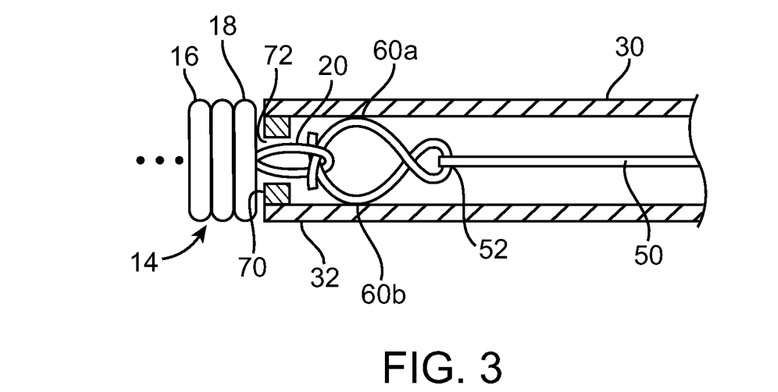
FIG. 3 is a partial cross-sectional view of the distal end of an elongate sheath. An occlusive element is secured to an elongate releasing member by a pair of retaining members.

FIGS. 2 and 3 illustrate an alternative embodiment of the delivery device 10. In this embodiment, two retaining members 60a, 60b are used to engage with the securing member 20 located on the proximal end 18 of the coil 14. In this embodiment, the two retaining members 60a, 60b may be formed from a common wire or filament as is shown in FIGS. 2 and 3. In this regard, the two retaining members 60a, 60b may be looped through a hole or loop (not shown) at the distal end 52 of the elongate releasing member 50. As best seen in FIG. 3, the retaining members 60a, 60b may have a pre-formed or natural configuration that naturally places the retaining members 60a, 60b in a closed configuration. The retaining members 60a, 60b may then be opened to release the securing member 20 and attached coil 14 by retracting the elongate releasing member 50 in the proximal direction. While the embodiment shown in FIGS. 2 and 3 illustrates two (2) retaining members 60a, 60b, alternative embodiments having additional retaining members 60 are also contemplated.

Figure 6:
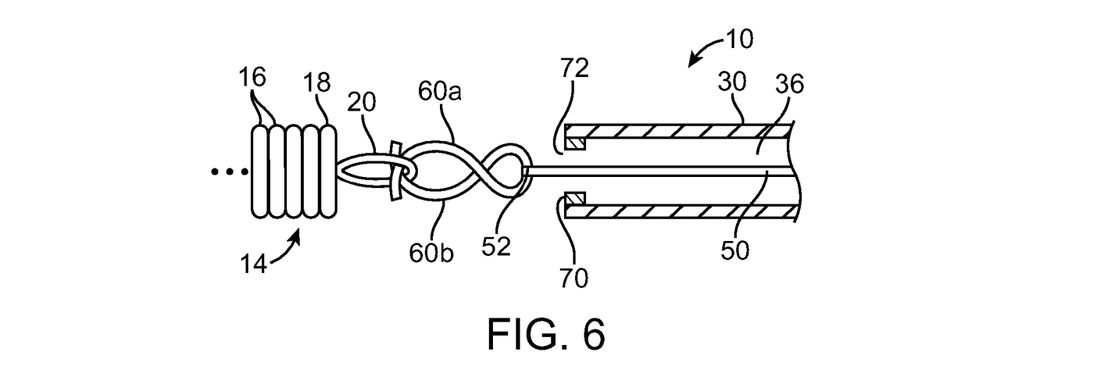
Figure 7:
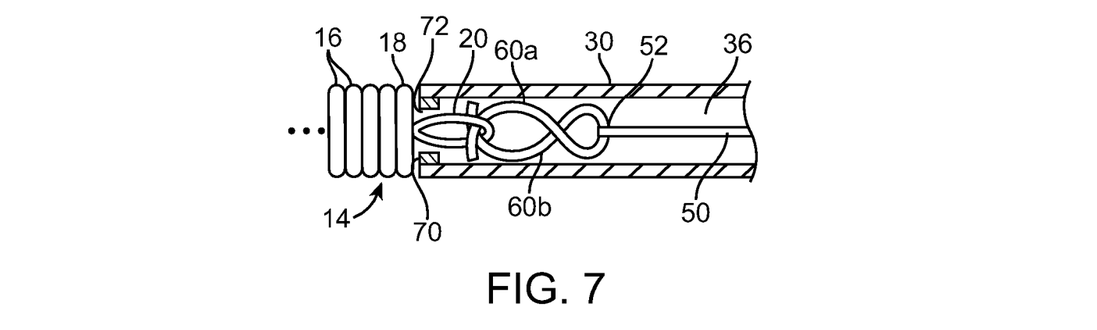
FIG. 7 illustrates the loading of the device shown in FIG. 6 after the coil is pushed proximally to load the securing member and retaining members within the lumen of the elongate sheath.

FIGS. 6-7, illustrate a process of loading the coil 14 to the delivery device 10. With reference to FIG. 6, the vaso-occlusive coil 14 is coupled with the delivery device 10. The elongate releasing member 50 is back loaded into the elongate sheath 30. The securing member 20 on the coil 14 is then coupled to the retaining members 60a, 60b. The coupling process may be accomplished by inserting the securing member 20 into the wires filaments forming the retaining members 60a, 60b. The wires or filaments may need to be flexed open to insert the securing member 20.

Next, as seen in FIG. 7, the coil 14 is then pushed proximally relative to the elongate sheath 30 to place the retaining members 60a, 60b within the lumen 36 of the elongate sheath 30. In addition, as shown in FIG. 7, the securing member 20 is at least partially contained within the lumen 36 of the elongate sheath 30. Depending on the size of the aperture 72, the wires or filaments forming the retaining member(s) 60 may need to flex to some degree to pass through aperture 72. FIG. 7 illustrates two retaining members 60a, 60b that are releasably coupled to the securing member 20. In the configuration illustrated in FIG. 7, the securing member 20 of the coil 14 is releasably locked to the elongate releasing member 50 via the two retaining members 60a, 60b. The coil 14 including the delivery system 10 may then be loaded into an introducer sheath (not shown).

Figure 8:
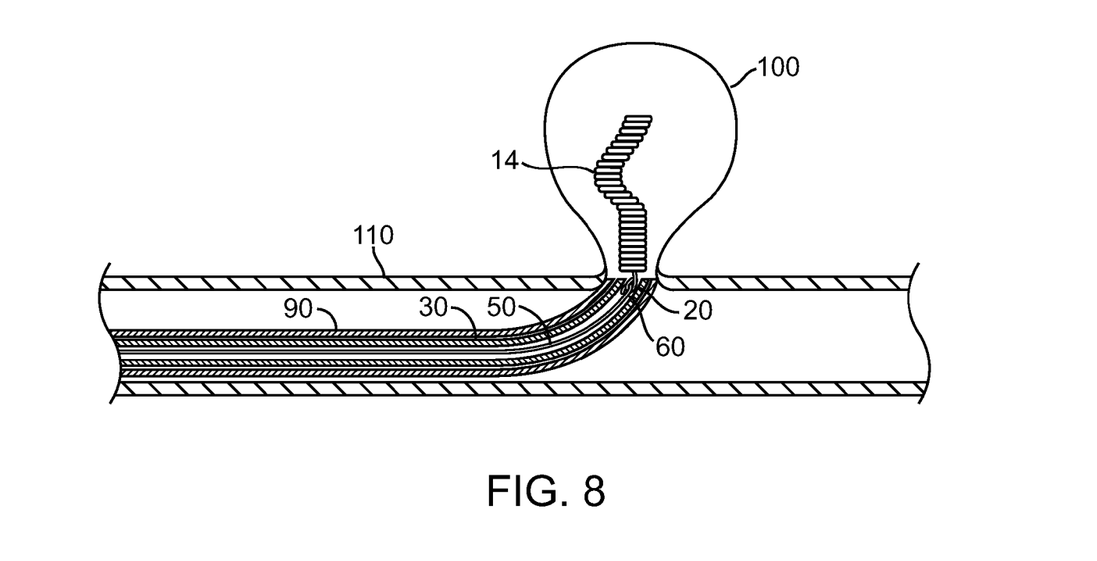
FIG. 8 is a cross-sectional view of a coil being delivered to an aneurysm using a delivery device of the type described herein.

FIG. 8 illustrates a process of delivering the coil 14 to an aneurysm 100 in a blood vessel 110. As seen in FIG. 8, a catheter 90 device such as a microcatheter is positioned within the vessel 110 so as to place the distal tip adjacent to the entry point or neck of the aneurysm 100. The device 10 of the type described herein is then advanced through the catheter 90. The device 10 is advanced to place the coil 14 in the aneurysm 100. One or more radiopaque markers (not shown) located on the catheter 90, elongate sheath 30, and/or elongate releasing member 50 may be used to aid the physician in positioning the device 10 for deployment of the coil 14. FIG. 8 illustrates the elongate releasing member 50 being coupled to the securing member 20 of the coil 14 via a single retaining member 60.

Figure 9:
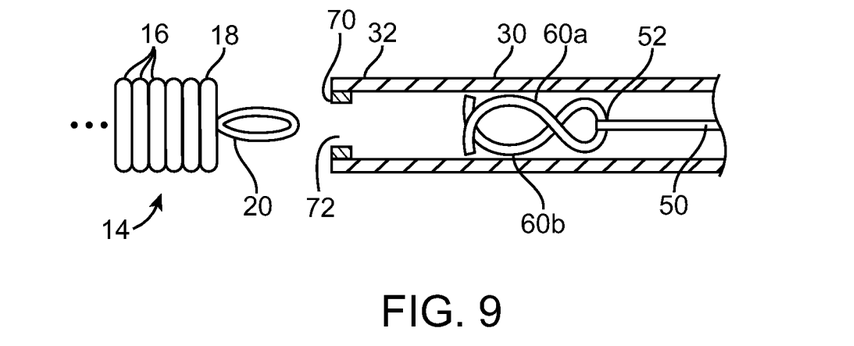

Next, with reference to FIG. 9, the elongate releasing member 50 is first separated from the elongate sheath 30 by unlocking the locking member 80 from the proximal end 34 of the elongate sheath 30. The elongate releasing member 50 is then pulled in the proximal direction with respect to the elongate sheath 30. As a proximal retraction force is applied to the elongate releasing member 50, the proximal end of the coil 18 will be stopped/blocked from entering the lumen 36 of the elongate sheath 30 by the blocking member 70. Moreover, the proximal retraction causes the retaining member(s) 60 to uncouple from the securing member 20 on the coil 14. For example, the wires or filaments forming the retaining member(s) 60 may flex or bend as the elongate releasing member 50 is pulled in the proximal direction. In one aspect, the wires or filaments forming the retaining member(s) 60 may be formed from a substantially elastic material so that the retaining members (s) 60 return to their original shape.

With the retaining member(s) 60 uncoupled from the securing member 20, the coil 14 is then fully released from the delivery device 10. The elongate sheath 30 and elongate releasing member 50 may then be retrieved from the body by withdrawing the elongate sheath 30 together with the elongate releasing member 50 in the proximal direction. If additional coils 14 need to be deployed, then another delivery device 10 (with attached coil assembly 14) may be advanced through the catheter 90 as described above. After all the coils 14 have been deployed, the catheter 90 is then withdrawn from the vessel 110.

One advantage of the delivery system 10 described herein is that a pull-to-release process is used to deploy the coil 14. Because a pulling motion is used, there is no risk of poking or puncturing the aneurysm 100 that is inherent in push-based delivery devices. In addition, because the coupling between the coil 14 and the elongate releasing member 50 is mechanical, detachment is faster than electrolytic-based delivery devices. Finally, the nature of coupling between the coil 14 and the elongate releasing member 50 produces a smooth release of the coil 14 during deployment.

While embodiments of the present invention have been shown and described, various modifications may be made without departing from the scope of the present invention.

The invention, therefore, should not be limited, except to the following claims, and their equivalents.

What is claimed is:

1. A delivery system for delivering an occlusive element to an implantation site in the vasculature system, comprising:
   an elongate sheath having a distal end and a proximal end and lumen extending between the distal and proximal ends;
   a distal blocking member located at the distal end of the elongate sheath, the distal blocking member including an aperture therein;
   an elongate releasing member disposed within the lumen of the elongate sheath, the elongate releasing member including a proximal end and a distal end, the distal end of the elongate releasing member terminating in first and second retaining members formed from a common filament or wire and having pre-formed configuration wherein the first and second retaining members include respective distal ends that overlap in the closed configuration;
   an occlusive element including a securing member positioned at a proximal end thereof and releasably secured to the first and second retaining members when the first and second retaining members are in the overlapping, closed configuration;
   wherein the securing member of the occlusive element passes through the aperture of the distal blocking member, and the first and second retaining members are released from the securing member by pulling on the elongate releasing member in a proximal direction,
   wherein the aperture of the distal blocking member is sized to prevent the releasing member from deploying out of the distal end of the elongate sheath and to prevent the occlusive element from moving proximally into the elongate sheath, and
   wherein the first and second retaining members comprise an elastic material configured to return to the overlapping, closed configuration after being released from the securing member.

2. The system of claim 1, wherein the first and second retaining members comprise a wire or filament looped through a hole disposed at the distal end of the elongate releasing member.

3. The system of claim 1, wherein the first and second retaining members and the elongate releasing member are formed from the same material.

4. The system of claim 1, further comprising a locking member disposed on a proximal region of the elongate releasing member.

5. The system of claim 4, wherein the locking member is releasably secured to the elongate sheath so as to prevent relative movement between the elongate releasing member and the elongate sheath.

6. The system of claim 1, wherein the securing member is bonded to the occlusive element.

7. The system of claim 1, wherein the elongate sheath is formed at least in part from hypotube.

8. The system of claim 1, wherein the elongate sheath is formed at least in part from a polymer material.

* * * * *